(12) United States Patent
Longson et al.

(10) Patent No.: US 7,803,142 B2
(45) Date of Patent: Sep. 28, 2010

(54) MICROTAPER NEEDLE AND METHOD OF USE

(75) Inventors: Matthew Stevens Longson, Holladay, UT (US); Dennis Joseph Griffin, Englewood, CO (US)

(73) Assignee: Summit Access LLC, Wilmington, DE (US)

( * ) Notice: Subject to any disclaimer, the term of this patent is extended or adjusted under 35 U.S.C. 154(b) by 824 days.

(21) Appl. No.: 11/343,663

(22) Filed: Jan. 31, 2006

(65) Prior Publication Data

US 2007/0060927 A1    Mar. 15, 2007

Related U.S. Application Data

(60) Provisional application No. 60/649,409, filed on Feb. 2, 2005.

(51) Int. Cl.
*A61M 5/32* (2006.01)
*A61M 5/178* (2006.01)
*A61F 11/00* (2006.01)

(52) U.S. Cl. .................. 604/272; 604/158; 606/108
(58) Field of Classification Search ............. 604/158, 604/272; 606/108
See application file for complete search history.

(56) References Cited

U.S. PATENT DOCUMENTS

| | | | | |
|---|---|---|---|---|
| 668,879 | A | * | 2/1901 | Miller .................. 27/21.1 |
| 2,269,963 | A | * | 1/1942 | Wappler .................. 604/61 |
| 3,877,429 | A | | 4/1975 | Rasumoff |
| 3,903,885 | A | | 9/1975 | Fuchs |
| 4,034,763 | A | | 7/1977 | Frazier |
| 4,166,469 | A | | 9/1979 | Littleford |
| 4,230,123 | A | | 10/1980 | Hawkins, Jr. |
| 4,239,042 | A | | 12/1980 | Asai |
| 4,243,050 | A | | 1/1981 | Littleford |
| 4,306,562 | A | | 12/1981 | Osborne |
| 4,405,314 | A | | 9/1983 | Cope |
| 4,414,983 | A | | 11/1983 | Evans et al. |
| 4,441,497 | A | | 4/1984 | Paudler |
| RE31,855 | E | | 3/1985 | Osborne |
| 4,538,622 | A | | 9/1985 | Samson et al. |
| 4,581,025 | A | | 4/1986 | Timmermans |
| 4,616,652 | A | | 10/1986 | Simpson |
| 4,650,472 | A | | 3/1987 | Bates |
| 4,693,250 | A | | 9/1987 | Coons |

(Continued)

OTHER PUBLICATIONS

US 6,645,204, 11/2003, Sharkey et al. (withdrawn)

*Primary Examiner*—Nicholas D Lucchesi
*Assistant Examiner*—Victoria P Campbell
(74) *Attorney, Agent, or Firm*—Workman Nydegger

(57) ABSTRACT

The present invention relates to medical needles used in connection with guide wires. A needle of the present invention includes a substantially cylindrical tube formed along a central longitudinal axis. A tapered tube is connected to one end of the tube and has a sharpened end. A channel extends through the cylindrical tube and the tapered tube, and is aligned with the longitudinal axis. In some embodiments, the tapered portion is radially expandable. For instance, radial expansion may result when a guide wire is selectively inserted through the channel. The radial expansion may be facilitated by a relief on the tapered tube portion. Optionally, the relief includes a plurality of slots which expand as a guide wire is inserted through the channel and tapered portion, thereby also causing the internal and outer diameters of the tapered portion to expand.

24 Claims, 5 Drawing Sheets

U.S. PATENT DOCUMENTS

| | | |
|---|---|---|
| 4,718,425 A | 1/1988 | Tanaka et al. |
| 4,721,506 A | 1/1988 | Teves |
| 4,731,052 A | 3/1988 | Seitz, Jr. |
| 4,737,146 A | 4/1988 | Amaki et al. |
| 4,772,266 A | 9/1988 | Groshong |
| 4,781,190 A | 11/1988 | Lee |
| 4,804,365 A | 2/1989 | Litzie et al. |
| 4,813,929 A | 3/1989 | Semrad |
| 4,826,481 A | 5/1989 | Sacks et al. |
| 4,830,023 A | 5/1989 | de Toledo et al. |
| 4,850,960 A | 7/1989 | Grayzel |
| 4,850,975 A | 7/1989 | Furukawa |
| 4,860,757 A | 8/1989 | Lynch et al. |
| 4,894,052 A | 1/1990 | Crawford |
| 4,917,094 A | 4/1990 | Lynch et al. |
| 4,919,653 A | 4/1990 | Martinez et al. |
| 4,934,380 A | 6/1990 | de Toledo |
| 4,952,870 A | 8/1990 | Strauer |
| 4,957,488 A | 9/1990 | Cameron et al. |
| 4,957,489 A | 9/1990 | Cameron et al. |
| 4,966,161 A | 10/1990 | Wallace et al. |
| 4,969,875 A | 11/1990 | Ichikawa |
| 4,973,305 A | 11/1990 | Goltzer |
| 4,979,956 A | 12/1990 | Silvestrini |
| 4,994,036 A | 2/1991 | Biscoping et al. |
| 4,994,040 A | 2/1991 | Cameron et al. |
| 4,995,878 A | 2/1991 | Rai |
| 4,998,912 A | 3/1991 | Scarbrough et al. |
| 5,011,473 A | 4/1991 | Gatturna |
| 5,059,183 A | 10/1991 | Semrad |
| 5,061,283 A | 10/1991 | Silvestrini |
| 5,078,745 A | 1/1992 | Rhenter et al. |
| 5,088,979 A | 2/1992 | Filipi et al. |
| 5,100,390 A | 3/1992 | Lubeck et al. |
| 5,114,401 A | 5/1992 | Stuart et al. |
| 5,129,889 A | 7/1992 | Hahn et al. |
| 5,134,031 A | 7/1992 | Kagechi et al. |
| 5,135,501 A | 8/1992 | Cameron |
| 5,141,494 A | 8/1992 | Danforth et al. |
| 5,149,329 A | 9/1992 | Richardson |
| 5,167,645 A | 12/1992 | Castillo |
| 5,186,179 A | 2/1993 | MacEachern |
| 5,190,528 A | 3/1993 | Fonger et al. |
| 5,232,442 A | 8/1993 | Johnson et al. |
| 5,242,410 A | 9/1993 | Melker |
| 5,242,427 A | 9/1993 | Bilweis |
| 5,255,691 A | 10/1993 | Otten |
| 5,256,146 A | 10/1993 | Ensminger et al. |
| 5,263,936 A | 11/1993 | Yurino |
| 5,263,938 A | 11/1993 | Orr et al. |
| 5,273,042 A | 12/1993 | Lynch et al. |
| 5,273,052 A | 12/1993 | Kraus et al. |
| 5,279,573 A | 1/1994 | Klosterman |
| 5,285,795 A | 2/1994 | Ryan et al. |
| 5,304,141 A | 4/1994 | Johnson et al. |
| 5,306,254 A | 4/1994 | Nash et al. |
| 5,334,210 A | 8/1994 | Gianturco |
| 5,358,490 A | 10/1994 | Henry et al. |
| 5,382,260 A | 1/1995 | Dormandy, Jr. et al. |
| 5,413,561 A | 5/1995 | Fischell et al. |
| 5,417,699 A | 5/1995 | Klein et al. |
| 5,423,770 A | 6/1995 | Yoon |
| 5,438,993 A | 8/1995 | Lynch et al. |
| 5,442,032 A | 8/1995 | Arnold et al. |
| 5,448,993 A | 9/1995 | Lynch et al. |
| 5,450,860 A | 9/1995 | O'Connor |
| 5,454,790 A | 10/1995 | Dubrul |
| 5,474,099 A | 12/1995 | Boehmer et al. |
| 5,489,273 A | 2/1996 | Whitney et al. |
| 5,490,845 A | 2/1996 | Racz |
| 5,492,530 A | 2/1996 | Fischell et al. |
| 5,507,301 A | 4/1996 | Wasicek et al. |
| 5,511,559 A | 4/1996 | Vance |
| 5,527,322 A | 6/1996 | Klein et al. |
| 5,558,635 A | 9/1996 | Cannon |
| 5,575,780 A | 11/1996 | Saito |
| 5,645,568 A | 7/1997 | Chervitz et al. |
| 5,662,603 A | 9/1997 | Gelbfish |
| 5,683,400 A | 11/1997 | McGuire |
| 5,703,200 A | 12/1997 | Bezwada et al. |
| 5,721,283 A | 2/1998 | Howard, Jr. et al. |
| 5,735,819 A | 4/1998 | Elliott |
| 5,762,639 A | 6/1998 | Gibbs |
| 5,779,719 A | 7/1998 | Klein et al. |
| 5,792,152 A | 8/1998 | Klein et al. |
| 5,807,304 A | 9/1998 | Cockburn |
| 5,807,311 A | 9/1998 | Palestrant |
| 5,810,012 A | 9/1998 | Lynch et al. |
| 5,810,810 A | 9/1998 | Tay et al. |
| 5,827,202 A | 10/1998 | Miraki et al. |
| 5,830,156 A | 11/1998 | Ali |
| 5,830,224 A | 11/1998 | Cohn et al. |
| 5,843,002 A | 12/1998 | Pecor et al. |
| 5,843,099 A | 12/1998 | Nichols et al. |
| 5,860,991 A | 1/1999 | Klein et al. |
| 5,861,015 A | 1/1999 | Benja-Athon |
| 5,885,227 A | 3/1999 | Finlayson |
| D408,530 S | 4/1999 | Eliasen et al. |
| 5,897,497 A | 4/1999 | Fernandez |
| 5,899,891 A | 5/1999 | Racz |
| 5,902,273 A | 5/1999 | Yang et al. |
| 5,911,710 A | 6/1999 | Barry et al. |
| 5,916,178 A | 6/1999 | Noone et al. |
| 5,922,024 A | 7/1999 | Janzen et al. |
| 5,932,299 A | 8/1999 | Katoot |
| 5,934,283 A | 8/1999 | Willem et al. |
| 5,971,957 A | 10/1999 | Luther et al. |
| 5,980,548 A | 11/1999 | Evans et al. |
| 5,997,523 A | 12/1999 | Jang |
| 6,004,279 A | 12/1999 | Crowley et al. |
| 6,011,988 A | 1/2000 | Lynch et al. |
| 6,012,457 A | 1/2000 | Lesh |
| 6,015,398 A * | 1/2000 | Arimatsu et al. ............ 604/272 |
| 6,024,740 A | 2/2000 | Lesh et al. |
| 6,033,720 A | 3/2000 | Stoltze et al. |
| 6,053,904 A | 4/2000 | Scribner et al. |
| 6,059,738 A | 5/2000 | Stoltze et al. |
| 6,063,085 A | 5/2000 | Tay et al. |
| 6,071,281 A | 6/2000 | Burnside et al. |
| 6,080,140 A | 6/2000 | Swaminathan et al. |
| 6,099,542 A | 8/2000 | Cohn et al. |
| 6,102,947 A | 8/2000 | Gordon |
| 6,117,101 A | 9/2000 | Diederich et al. |
| 6,117,535 A | 9/2000 | Szycher et al. |
| 6,120,480 A | 9/2000 | Zhang et al. |
| 6,120,496 A | 9/2000 | Whayne et al. |
| 6,120,500 A | 9/2000 | Bednarek et al. |
| 6,126,633 A | 10/2000 | Kaji et al. |
| 6,136,015 A | 10/2000 | Kurz et al. |
| 6,139,540 A | 10/2000 | Rost et al. |
| D433,503 S | 11/2000 | Powers et al. |
| 6,142,994 A | 11/2000 | Swanson et al. |
| 6,164,283 A | 12/2000 | Lesh |
| 6,168,611 B1 | 1/2001 | Rizvi |
| 6,171,286 B1 | 1/2001 | Gross |
| 6,179,828 B1 | 1/2001 | Mottola et al. |
| 6,203,556 B1 | 3/2001 | Evans et al. |
| 6,206,893 B1 | 3/2001 | Klein et al. |
| 6,210,366 B1 | 4/2001 | Sanfilippo, II |
| 6,214,022 B1 | 4/2001 | Taylor et al. |
| 6,228,052 B1 | 5/2001 | Pohndorf |
| 6,238,355 B1 | 5/2001 | Daum |
| 6,241,710 B1 | 6/2001 | VanTassel et al. |
| 6,245,064 B1 | 6/2001 | Lesh et al. |

| | | | | | | |
|---|---|---|---|---|---|---|
| 6,254,599 | B1 | 7/2001 | Lesh et al. | 6,579,246 B2 | 6/2003 | Jacobsen et al. |
| 6,267,760 | B1 | 7/2001 | Swanson | 6,585,638 B1 | 7/2003 | Yamamoto |
| 6,272,370 | B1 | 8/2001 | Gillies et al. | 6,595,989 B1 | 7/2003 | Schaer |
| 6,305,378 | B1 | 10/2001 | Lesh | 6,599,288 B2 | 7/2003 | Maguire |
| 6,306,153 | B1 | 10/2001 | Kurz et al. | 6,605,062 B1 | 8/2003 | Hurley et al. |
| 6,312,374 | B1 | 11/2001 | Von Hoffmann | 6,607,502 B1 | 8/2003 | Maguire et al. |
| 6,322,571 | B1 | 11/2001 | Adams | 6,626,916 B1 | 9/2003 | Yeung et al. |
| 6,332,874 | B1 | 12/2001 | Eliasen et al. | 6,635,022 B2 | 10/2003 | Berg et al. |
| 6,356,791 | B1 | 3/2002 | Westlund et al. | 6,638,276 B2 | 10/2003 | Sharkey et al. |
| 6,383,151 | B1 | 5/2002 | Diederich et al. | 6,652,515 B1 | 11/2003 | Maguire et al. |
| 6,398,743 | B1 | 6/2002 | Halseth et al. | 6,652,542 B2 | 11/2003 | Blatter et al. |
| 6,416,499 | B2 | 7/2002 | Paul, Jr. | 6,669,709 B1 | 12/2003 | Cohn et al. |
| 6,416,505 | B1 | 7/2002 | Fleischman et al. | 6,692,494 B1 | 2/2004 | Cooper et al. |
| 6,416,511 | B1 | 7/2002 | Lesh et al. | 6,695,782 B2 | 2/2004 | Ranucci et al. |
| 6,419,641 | B1 | 7/2002 | Mark et al. | 6,702,790 B1 | 3/2004 | Ross et al. |
| 6,419,673 | B1 | 7/2002 | Edwards et al. | 6,702,972 B1 | 3/2004 | Markle |
| 6,425,895 | B1 | 7/2002 | Swanson et al. | 6,726,694 B2 | 4/2004 | Blatter et al. |
| RE37,815 | E | 8/2002 | Rizvi | 6,733,496 B2 | 5/2004 | Sharkey et al. |
| 6,447,507 | B1 | 9/2002 | Bednarek et al. | 6,758,830 B1 | 7/2004 | Schaer et al. |
| 6,458,088 | B1 | 10/2002 | Hurtak et al. | 6,758,847 B2 | 7/2004 | Maguire |
| 6,468,248 | B1 | 10/2002 | Gibbs | 6,772,012 B2 | 8/2004 | Ricart et al. |
| 6,471,689 | B1 | 10/2002 | Joseph et al. | 6,773,417 B2 | 8/2004 | Fitzgibbons et al. |
| 6,475,135 | B1 | 11/2002 | Levy | 6,780,183 B2 | 8/2004 | Jimenez, Jr. et al. |
| 6,477,402 | B1 | 11/2002 | Lynch et al. | 6,786,905 B2 | 9/2004 | Swanson et al. |
| 6,482,224 | B1 | 11/2002 | Milchler et al. | 6,790,220 B2 | 9/2004 | Morris et al. |
| 6,485,413 | B1 | 11/2002 | Boppart et al. | 6,799,075 B1 | 9/2004 | Chornenky et al. |
| 6,488,662 | B2 | 12/2002 | Sirimanne | D498,844 S | 11/2004 | Diamond et al. |
| 6,500,174 | B1 | 12/2002 | Maguire et al. | 6,811,544 B2 | 11/2004 | Schaer |
| 6,502,576 | B1 | 1/2003 | Lesh | 6,852,110 B2 | 2/2005 | Roy et al. |
| 6,514,271 | B2 | 2/2003 | Evans et al. | 6,866,662 B2 | 3/2005 | Fuimaono et al. |
| 6,517,553 | B2 | 2/2003 | Klein et al. | 6,872,205 B2 | 3/2005 | Lesh et al. |
| 6,522,930 | B1 | 2/2003 | Schaer et al. | 6,878,155 B2 | 4/2005 | Sharkey et al. |
| 6,537,266 | B1 | 3/2003 | Mottola et al. | 6,907,992 B2 | 6/2005 | McMichael et al. |
| 6,551,281 | B1 | 4/2003 | Raulerson et al. | 6,939,353 B2 | 9/2005 | Que et al. |
| 6,551,334 | B2 | 4/2003 | Blatter et al. | 6,945,964 B2 | 9/2005 | Ross et al. |
| 6,562,052 | B2 | 5/2003 | Nobles et al. | 2004/0030319 A1 | 2/2004 | Korkor et al. |
| 6,565,542 | B2 | 5/2003 | Kumar et al. | | | |

* cited by examiner

MICROTAPER NEEDLE AND METHOD OF USE

CROSS-REFERENCE TO RELATED APPLICATIONS

This application claims the benefit of U.S. Provisional Patent Application No. 60/649,409, filed on Feb. 2, 2005, and entitled "MICROTAPER NEEDLE", which is incorporated herein by reference in its entirety.

BACKGROUND OF THE INVENTION

1. The Field of the Invention

Exemplary embodiments of the invention relate to the field of vascular access devices and methods. More particularly, the invention relates to apparatus and methods for efficiently obtaining vascular access in a manner that limits blood loss by patient.

2. The Relevant Technology

An important element in any medical procedure is the control and reduction of blood lost by the subject (i.e. patient) of the procedure. Stopping blood loss is a particular concern in intravascular procedures where a laceration is made in a vein or artery so as to grant venous or arterial access. Commonly, these procedures involve the insertion, use, and removal of a guide wire, catheter, and/or other medical device to diagnose or attempt repair of a condition within the artery or vein. Intravascular procedures of this type represent a significant number of medical procedures performed each year—well into the hundreds of thousands on human patients alone—thus providing at least an equal number of procedures where blood loss is a concern for human as well as animal patients.

Accessing a vein, artery or bodily cavity typically requires entrance through a wall of the vein, artery or cavity (collectively referred to herein as "blood vessels" or "vessels"), which further requires that an access site be selected and the vessel wall be lacerated or punctured. The size of this access site is of particular concern. In general, the larger the access site, the greater the amount of blood that may escape therefrom into the surrounding body cavities and tissue. Where excessive blood is lost, the effectiveness of the medical procedure may be compromised and complications may arise.

One method to avoid or reduce the risk of excess blood loss is to reduce the size of the vascular access site. In a method commonly referred to as "micropuncture", a multi-step process is performed to give a physician vascular access through a small access site. Generally, the physician uses a 21 gauge (0.032 inch) hypodermic needle to access the blood vessel, and a 0.018 inch guide wire is thereafter inserted into the vessel through the needle. With the guide wire in place, the needle may then be extracted from the vessel, leaving the guide wire in place.

Next, the physician places a coaxial dilator over the guide wire and inserts the dilator into the patient's vessel. The vascular wall is flexible and resilient. Accordingly, as the dilator is inserted, the initial incision is stretched to accommodate the dilator. Thus, the dilator may have an outer diameter that exceeds the initial diameter of the access site, as well as the needle used to make the access site. With the coaxial dilator in place, the guide wire and the inner dilator may be removed. The outer dilator has an internal diameter sufficient to accommodate a 0.035 inch guide wire which is then inserted. Upon insertion, the physician can then use the inserted guide wire to insert and position a catheter in a patient's vasculature. Most commonly, the catheter has a inner diameter of 0.035 inch or 0.038 inch. Once the procedure is complete, the catheter and guide wire may be removed. The access site in the vascular wall then returns to about its original size, thus reducing the patient's blood loss and recovery time.

While the micropuncture system provides vascular access in a manner that reduces blood loss and recovery time, it involves a variety of medical devices and procedures. For instance, as described above, the micropuncture system involves multiple steps and instruments. Accordingly, a need exists for devices and methods for obtaining vascular access with a reduced complexity and a reduced number of medical instruments.

BRIEF SUMMARY OF THE INVENTION

Exemplary embodiments of the invention relate to an apparatus and a method for accessing a blood vessel in a manner that limits the size of a corresponding vascular access site, while also allowing expansion of the vascular access site to receive larger medical devices such as guide wires and catheters. A needle with a tapered cutting end may create a vascular access site. Thereafter, a guide wire may be pushed through the needle and expand the tapered cutting end which temporarily stretches the vascular walls.

For example, in one embodiment, a needle of the present invention includes a substantially cylindrical tube formed along a central longitudinal axis. A tapered tube is connected to one end of the tube and has a sharpened end. A channel extends through the cylindrical tube and the tapered tube, and is aligned with the longitudinal axis. In some embodiments, the tapered portion is radially expandable. For instance, radial expansion may result when a guide wire is selectively inserted through the channel. The radial expansion may be facilitated by a relief on the tapered tube portion. Optionally, the relief includes a plurality of slots which expand as a guide wire is inserted through the channel and tapered portion, thereby also causing the internal and outer diameters of the tapered portion to expand.

In some additional embodiments, a medical needle comprises a substantially cylindrical tube and a tapered distal tube adjacent to and concentric with the cylindrical tube. Further, the medical needle may include a cutting tip at the distal end of the tapered tube, and a relief in the tapered tube for facilitating expansion of at least one diameter of the cutting tip. The outside diameter of the cylindrical tube may be greater than the outside diameter of the cutting tip. The relief may include one or more portions which, in some embodiments, are elongated slots formed in at least the tapered tube. One elongate slot may intersect a cutting surface of the cutting tip, while one or more additional slots may be offset from the cutting surface. The width of the slots can increase as a guide wire is inserted into the needle, and thus also deforming the tapered distal tube by increasing its outer and internal diameters.

In other embodiments, a method for inserting a medical device into a body cavity of a subject is described. A substantially tubular needle may be inserted into a body cavity and may have an internal passageway therethrough, as well as a sharpened distal end having a first internal diameter. A guide wire having an outer diameter greater than the first internal diameter may be inserted into the internal passageway. The sharpened distal end may be expanded to have a second internal diameter sufficient to allow the guide wire to pass through the sharpened distal end. Thereafter, the guide wire may be used to insert a medical device into a body cavity. Before the medical device is inserted, the needle may be optionally removed.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope, nor are the drawings necessarily drawn to scale. The invention will be described and explained with additional specificity and detail through the use of the accompanying drawings in which.

DETAILED DESCRIPTION OF THE PREFERRED EMBODIMENTS

Figure 1:
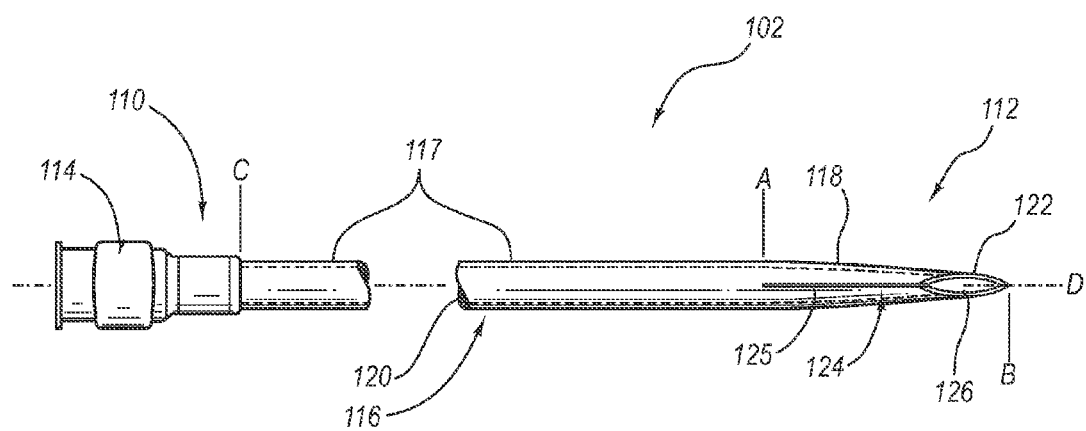
FIG. 1 is a top view of an expandable needle according to one embodiment of the present invention, the expandable needle having a substantially cylindrical tube mounted to a tapered portion.

Exemplary embodiments of the present invention relate to apparatus and methods for efficiently accessing a blood vessel to insert a catheter. One feature of the embodiment is an expandable needle that creates a small incision in a vascular wall. Thereafter, the needle expands and temporarily stretches the incision in the vascular, and allows a larger guide wire usable with a standard sized catheter to be inserted therein. In this manner, medical procedures in which a catheter is installed can be performed quickly and efficiently, and hemostasis of the patient is promoted. In particular, only a small vascular incision need be made, thereby reducing blood loss, while a single guide wire, usable with a standard-sized catheter, provides access for catheter placement.

Reference will now be made to the drawings to describe various aspects of exemplary embodiments of the invention. It is understood that the drawings are diagrammatic and schematic representations of such exemplary embodiments, and are not limiting of the present invention, nor are they necessarily drawn to scale. No inference should therefore be drawn from the drawings as to the dimensions of any invention or element. In the following description, numerous specific details are set forth in order to provide a thorough understanding of the present invention. It will be obvious, however, to one of ordinary skill in the art that the present invention may be practiced without these specific details. In other instances, well-known aspects of catheters, guide wires, and needles, and methods for using the same, have not been described in particular detail in order to avoid unnecessarily obscuring the present invention.

For convenience, it is noted that the medical industry has adopted a wide variety of measurement systems for use with different medical devices. For example, needles are commonly measured according to needle wire gauge, which is based off the Birmingham (Stub's Iron) wire gauge, and takes into account the outer diameter of the needle. In contrast, guide wires are measured according to an outer diameter in English units of 1000th of an inch. In yet another measurement system, an outer diameter of a catheter, and a sheath or dilator, is measured in millimeters, which is recited as a French (Fr.) size. Commonly, the inner diameter of a catheter, sheath or dilator is measured in English units of 1000th of an inch to reflect compatible guide wires.

For consistency, where size measurements are herein provided for needles, guide wires, catheters, sheaths, and the like, a measurement system based on English units to the 1000th of an inch will be used. However, where possible, and to be consistent with accepted medical measurement systems, an approximate measurement in a conventional gauge or French size is also indicated. Accordingly, as used herein, the term "gauge" will refer to needle wire gauge based off the Birmingham (Stub's Iron) wire gauge. In addition, and except as otherwise noted any measurement to the 1000th of an inch includes tolerances of ±0.001 inch. Similarly, any measurement to the 10,000th of an inch includes tolerances of ±0.0001 inch.

With reference to FIG. 1, a hypodermic needle 102 is illustrated in accordance with one embodiment of the present invention. In this embodiment, hypodermic needle 102 includes a substantially cylindrical tube 116 having a proximal end 110 and a distal end 112, a hub 114 mounted to proximal end 110, and a cutting tip 122 at distal end 112. Such a combination allows, for example, hypodermic needle 102 to create an incision in the patient's skin or tissue while also being easily attachable to a syringe or other medical device for either insertion or extraction of a fluid or medical instrument.

To further facilitate insertion or extraction of fluids or medical instruments, cylindrical tube 116 includes an internal passageway 120 configured to receive a transferred fluid or a medical instrument. In the illustrated embodiment, for example, cylindrical tube 116 includes a straight tubular portion 117 integrally formed with a tapered tubular portion 118, and an internal passageway 120 centered in both straight portion 117 and tapered portion 118. As illustrated, a straight, longitudinal axis D is centered in, and extends through, hypodermic needle 102, including straight portion 117 and tapered portion 118. In this manner, internal passageway 120 also follows longitudinal axis D and is concentric therewith.

As illustrated, an exemplary straight portion 117 is connected to tapered portion 118 at junction A and to hub 114 at junction C. In addition, straight portion 117 may be straight and have a constant diameter. For instance, in one embodiment, and by way of representation and not limitation, straight portion 117 has an outer diameter of 0.049 inch (18 gauge). In other embodiments, straight portion 117 may have other diameters including, for example, outer diameters at or between 0.032 inch (21 gauge) and 0.072 inch (15 gauge).

The internal diameter of straight portion 117 may similarly be varied. For example, the internal diameter of straight portion 117 may vary between 0.024 inch and 0.064 inch. In one embodiment, for instance, where the outer diameter of straight portion 117 is 0.049 inch, the internal diameter is between 0.036 inch and 0.043 inch. One feature of an internal diameter of this size is that a standard guide wire may be easily inserted and passed through the interior of straight portion 117. A standard 0.035 inch guide wire may be inserted into internal passageway 120. Inasmuch as the diameter of passageway 120 in straight portion 117 (e.g. the internal diameter of straight portion 117) is greater than the diameter of the guide wire, a minimal force is required to push the guide wire through straight portion 117.

While straight portion 117 is illustrated as being straight and having a constant internal and external diameter, it will be appreciated that these features are exemplary only. For instance, it is contemplated that, in some embodiments, cylindrical tube 116, including straight portion 117 are curved or bent. In such an embodiment, longitudinal axis D and internal passageway 120 may remain centered within straight portion 117 and, accordingly, may also be curved or bent. Similarly, the internal and external diameters may vary along the length of straight portion 117 and/or passageway 120 may be offset so as to not be centered within straight portion 117.

Connected to straight portion 117 is tapered tubular portion 118. Tapered portion 118 is configured to reduce the size of a vascular access site created upon insertion of needle 102 into a blood vessel or body cavity, while also allowing a larger guide wire to be inserted therethrough. In the illustrated embodiment, for example, the tapered portion 118 may narrow as tapered portion 118 extends from junction A to cutting tip 122. In this manner, the outer diameter of tapered portion 118 at cutting tip 122 is less than the outer diameter at junction A. Accordingly, as cutting tip 122 makes an incision to create a vascular access site, the incision has approximately the same diameter as the diameter of cutting tip 122. Thereafter, tapered tubular portion 118 or a larger medical device is inserted into the blood vessel, the vascular walls can stretch and expand to accommodate a larger diameter, without permanently increasing the size of the vascular access site.

For instance, in the exemplary embodiment described above, the outer diameter of cylindrical tube 116 at junction A may be 0.049 inch (18 gauge). Tapered portion 118, however, decreases in diameter as it approaches cutting tip 122. At cutting tip 122, the outer diameter may be decreased to, for example, 0.016 inch (27 gauge) and 0.042 inch (19 gauge), such as, for example, 0.032 inch (21 gauge). Correspondingly, an interior diameter at cutting tip 122 may also be decreased. For instance, the interior diameter at cutting tip 122 may measure at or between 0.008 inch and 0.034 inch.

The length of tapered portion 118 may vary based on any of a variety of factors. For instance, based on the diameters of straight portion 117 and cutting tip 122, and the change in diameter therebetween, a larger or smaller taper may be desired. Additionally, the length may be varied based on a physician's preference, the vessel to be accessed, or patient-specific factors such as the tissue or vascular wall thickness. In still other embodiments, and as discussed in more detail with respect to FIGS. 3A and 3B, the length of tapered portion 118 may affect the opening force required for distal end 112. Accordingly, tapered portion 118 may, be manufactured or produced in any of a variety of lengths based on physician preferences, medical procedures being performed, or to accommodate patient factors. For instance, in one example, where tapered portion narrows from 0.049 inch (18 gauge) to 0.032 inch (21 gauge), a relatively short tapered portion may be created having a major length (i.e. from Junction A to Point B) of 0.367±0.01 inch. Alternatively, tapered portion 118 may have a medium major length such as, for example, 0.551±0.01 inch, or a longer major length such as, for example, 0.734±0.01 inch.

Hypodermic needle 102 may be produced of any suitable material well known in the art. For instance, cylindrical tube 116 may be produced from metals, composites, or plastics. By way of example, representative materials may include medical grade steel, stainless steel, nitinol, or other metals or alloys (including shape memory alloys).

Tapered portion 118 may be produced by any suitable method. For instance, cylindrical tube 116 may be formed by molding or casting. Alternatively, substantially cylindrical tube 116 may be formed by initially forming a tube having a constant diameter. Thereafter, a cold working or similar process may be used to create tapered portion 118. For instance, a mandrel may be inserted into passageway 120. Thereafter, cylindrical tube 116 may be forced against a die to create tapered portion 118, while heat is added or even in the absence of additional heat. In an alternative embodiment, a milling or grinding process is used so as to form tapered portion 118. In still another embodiment, tapered portion 118 is formed separate from straight portion 117 and is thereafter mechanically fastened to straight portion 117 by a welding or other suitable process. It will be appreciated, therefore, that whether mechanically fastened or integrally formed, straight portion 117 and tapered portion 118 are properly considered to be connected.

In some embodiments, hypodermic needle 102 is configured to allow a guide wire or other medical instrument to extend through all or a portion of internal passageway 120. In some embodiments, the outer diameter of the guide wire inserted therethrough is greater than the internal diameter of all or a substantial portion of tapered tubular portion 118, including cutting tip 122.

For instance, consider an exemplary embodiment in which a 0.035 inch guide wire is inserted into the passageway of a hypodermic needle having a tapered tubular portion which narrows from an internal diameter of 0.042 inch to an internal diameter of 0.019 inch at the cutting tip. As will be appreciated, because the guide wire has an outer diameter greater than an internal diameter of the tapered portion, it will be difficult to extend the guide wire fully through the tapered portion unless a relief is provided.

Accordingly, in one embodiment of the present invention, hypodermic needle 102 includes a relief 124 at tapered portion 118. Relief 124 is configured to allow the internal diameter of tapered tubular portion 118 to expand and receive a guide wire with a diameter greater than the initial, unexpanded internal diameter of the guide wire.

In the illustrated embodiment, relief 124 may comprise a slot 125 formed in tapered tubular portion 118. In one example, slot 125 extends through the wall of tapered portion 118, and along its full length (i.e., from junction A to cutting surface 126 of cutting tip 122). In this manner, and as will be discussed in greater detail with respect to FIGS. 3A and 3B, as a guide wire is inserted into tapered portion 118, it exerts radial forces against an interior surface of tapered tubular portion 118, thereby causing selective, radial expansion of tapered portion 118. Thus, relief 124 facilitates radial expansion of tapered portion 118 in response to insertion of a guide wire.

Returning again to FIG. 1, in some embodiments, hypodermic needle 102 includes hub 114 mounted to proximal end 110, such that a junction C is formed between hub 114 and cylindrical tube 116. While the illustrated embodiment depicts hub 114 as being directly mounted to cylindrical tube 116, it will be appreciated that this is not necessary, and that hub 114 may also be indirectly mounted thereto. Hub 114 may further be configured to allow medical personnel or another user to quickly and efficiently connect hypodermic needle 102 to a syringe (not shown) or other medical device. For instance, a syringe may include a chamber housing a fluid for injection into the tissue or a body cavity of a patient, or may be empty so as to receive a fluid (e.g., blood) from the patient. In this manner, a fluid passes through passageway 120 either into, or out from, the body of the patient. Accordingly, hub 114 is properly considered a means for connecting hypodermic needle 102 to a syringe or other fluid injection or extraction device.

Hub 114 may be made of any suitable material. For instance, hub 114 may be made of the same or a similar material as cylindrical tube 116. Accordingly, hub 114 may be integrally manufactured with cylindrical tube 116 or may be fused, welded, or otherwise affixed thereto. In yet another embodiment, hub 116 is a polymeric material which may be molded (e.g., by injection or insertion molding) to cylindrical tube 116.

Figure 2:
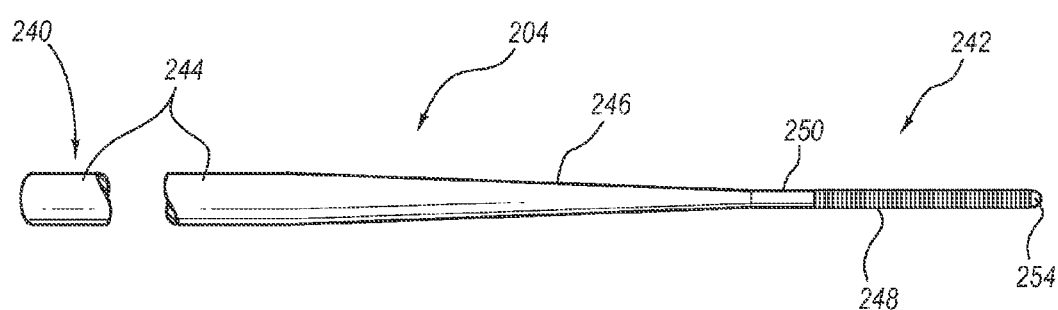
FIG. 2 is a side view of a tapered guide wire according to one embodiment of the present invention.

Referring now to FIG. 2, an exemplary embodiment of a guide wire 204 is illustrated. Guide wire 204 is one embodiment of a guide wire for insertion into a patient's blood vessel and which may radially expand a hypodermic needle such as hypodermic needle 102 of FIG. 1, and which may be used to facilitate insertion of a catheter or other medical device. Guide wire 204 may be made of any of a variety of materials well known in the art including, for example, stainless steel, nitinol, or any other suitable material. In addition, guide wire 204 may be fully or partially coated with, for example, Teflon or a hydrophilic polymer.

In the illustrated embodiment, guide wire 204 includes a wire body 244 having a constant, first diameter, a coil 248 having a second, smaller diameter, and a tapered section 246 which narrows from the first diameter of wire body 244 to the smaller diameter of coil 248. As will be appreciated, particularly in light of the disclosure herein, one feature of guide wire 204 which includes tapered section 246 between a larger body and smaller coil is that guide wire 204 may be used when a small vascular access site is created and when a catheter or other medical device is inserted. In this manner, the number of medical devices and the time necessary to perform a medical procedure are reduced.

For instance, coil 248 may have an outer diameter equal to or smaller than the internal diameter of a needle such as needle 102 (FIG. 1). As an example, if needle 102 has an internal diameter of 0.019 inch, the outer diameter of coil 248 may be equal to or less than 0.019 inch (e.g., 0.018 inch). In this manner, where coil 248 is positioned at distal end 242 of guide wire 204, the coil may easily be pushed through a needle and into a blood vessel.

As is further illustrated, tapered section 246 extends between wire body 244 and coil 248. Wire body 244 is positioned at proximal end 240 of guide wire 204 and may be of a standard size used in medical procedures. For instance, guide wire 244 may be adapted for a catheterization procedure, and wire body 244 may have an outer diameter of 0.035 inch. Accordingly, in this example, tapered section 246 narrows guide wire 204 from 0.035 inch diameter to a 0.019 inch diameter. Stated another way, tapered section 246 reduces the diameter of guide wire 204 from a diameter usable for a medical procedure to a diameter usable when creating a small vascular access site.

Another feature of tapered section 246 is realized when guide wire 204 is used with an expandable, tapered needle (e.g., needle 102). As will be appreciated in light of the disclosure herein, where the internal diameter of a needle distal tip is less than the outer diameter of wire body 244, an opening force may be required so as to radially expand the needle distal tip to accommodate larger wire body 244. Where tapered section 246 provides for a gradual increase in diameter as wire body 244 approaches the needle distal tip, the opening force is distributed over time. Accordingly, tapered section 246 may be of any desired length so as to distribute the opening force necessary to expand a medical needle. For instance, tapered section 246 may increase the diameter of guide wire 204 over a length of 0.5 to 6 inches. In other embodiments, it will be appreciated that the guide wire does not have a taper, or the length of the taper is less than 0.5 inch or greater than 6 inches.

As is further illustrated, tapered section 246 may not be directly connected to coil 248. In the illustrated embodiment, for example, an interface 250 is included between coil 248 and tapered section 246. In this embodiment, the diameter of interface 250 is approximately equal to the diameter of coil 248, although in other embodiments the diameter of interface 250 is greater or less than the diameter of coil 248. In still other embodiments, the diameter of interface 250 may vary over its length. For instance, in one embodiment, the diameter of interface 250 is equal to the diameter of a core wire extending through coil 248. Accordingly, in some embodiments, the diameter of tapered section 246 expands from the diameter of interface 250 to the diameter of wire body 244.

In some embodiments, guide wire 204 is further configured for quick and easy extension through a medical needle. For instance, tapered section 246 may be polished, coated or lubricated so as to reduce friction with the medical needle. This may be particularly useful where, for example, tapered section 246 is created by a precision grinding or milling. In such a process, ridges, burs, paddles, steps, or tapers may be formed, each of which potentially increase friction between guide wire 204 and a corresponding needle.

As discussed previously, a coil 248 may be included at distal end 242 of guide wire 204. Coil 248 may be, for example, a platinum coiled soft tip. In addition, a solder ball 254, as known in the art may be included at the end of coil 248. Further, a core wire (not shown) may also be included at distal end 242 and positioned under coil 248. In some additional embodiments, a j-hook as known in the art is formed in coil 248.

The length and diameter of coil 248 may be varied, based on at least the application and procedure to be performed. For instance, in one embodiment, it is contemplated that the length of coil 248 is at or between approximately 2 and 3 inches.

Figure 3A:
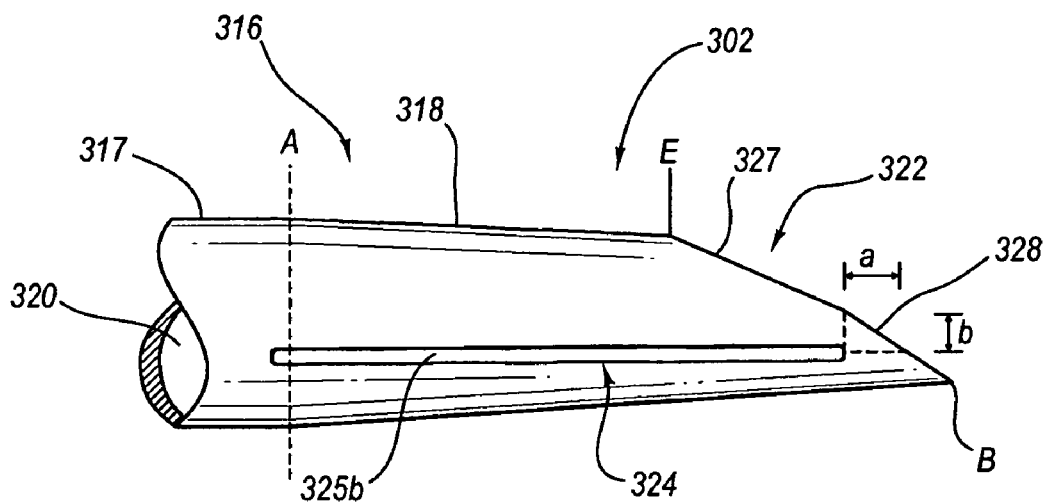
FIG. 3A is a side view of the distal end of a tapered needle having a relief to facilitate radial expansion of the distal end, according to one embodiment of the present invention.
Figure 3B:
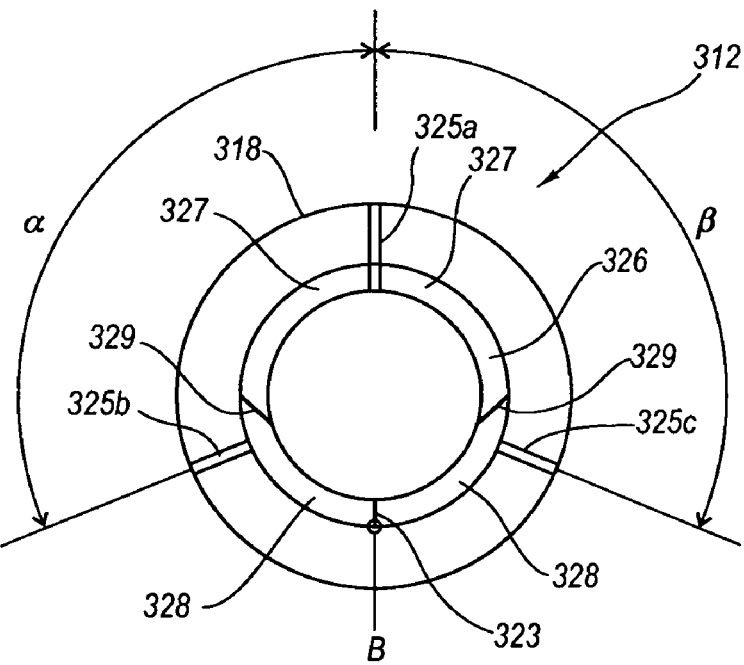
FIG. 3B is a frontal view of the cutting tip of the needle of FIG. 3A.

Now referring to FIGS. 3A and 3B, an exemplary tapered needle 302 includes, in one embodiment, a relief 324 for facilitating expansion of a tapered portion 318 of the distal end 312 of needle 302. As discussed previously, a needle such as needle 302 may be configured to create a small vascular access site (e.g. less than the diameter of a guide wire used to insert a catheter). Thus, one feature of relief 324 is that needle 302 may create a small vascular access site while also allowing for a larger guide wire (e.g., guide wire having a larger outer diameter than the unexpanded diameter of a cutting tip 322) to pass therethrough for insertion of a catheter or other medical device. In this manner, a physician may insert only a single, larger guide wire while also creating a small vascular access site.

In the illustrated embodiment, relief 324 comprises a plurality of slots 325a-325c formed in tapered portion 318. Slots 325a-c are configured so as to provide relief such that as a guide wire is pushed through passageway 320, the internal diameter of tapered portion 318 can increase to accommodate the larger diameter guide wire. In particular, as a guide wire is pushed into passageway 320, any portion of the guide wire having a diameter equal to or less than the diameter of passageway 320 at cutting tip 320 can pass through with minimal difficulty. However, a guide wire or portion of a guide wire having a larger diameter will encounter considerable resistance unless relief 324 relieves that resistance.

In one embodiment, needle 302 is configured such that as a larger diameter guide wire is pushed through needle 302, the guide wire exerts forces against the internal surface of tapered portion 318. Slots 325a-c are configured to relieve by allowing tapered portion 318 to expand in a radial direction. In particular, the sizes of slots 325a-c increase, thereby facilitating radial expansion of tapered portion 318.

As may be appreciated in light of the disclosure herein, a force must be applied to the guide wire to expand tapered portion 318 so as to allow a larger wire body of the guide wire through the smaller tapered portion 318 and cutting tip 322. As used herein, this force is referred to as an opening force.

The opening force is important for a variety of reasons. For instance, a greater required opening force means that an operating physician will have greater difficulty in inserting the guide wire into the vasculature. In addition, if a large resistance is initially encountered, the physician may exert a large force that overcomes the resistance but cannot be sufficiently controlled. This may be detrimental in that the guide wire may be inserted to quickly and be mispositioned, or the guide wire may be detrimentally forced into a vascular wall.

Accordingly, the present invention may be configured to reduce the opening force so as to allow a physician to insert the guide wire with a reduced risk of vascular damage or mispositioning of the guide wire. For example, needle 302 may be configured to have an opening force between 0.0 and 2.5 pounds. More specifically, needle 302 may be configured to have an opening force of 1.0±0.5 pound.

A variety of factors influence the necessary opening force required. For instance, the size and type of guide wire is one consideration. In addition, the material used in manufacturing needle 302 may also affect the required opening force, as may the manufacturing process. For instance, where needle 302 is made of medical quality steel and is manufactured by cold working needle 302 to form tapered portion 318 (e.g., with a mandrel and die), residual stresses may be created that resist radial expansion. In addition, the polished surface of passageway 320 and/or the guide wire may reduce the friction and thus also the needed opening force, while uneven surfaces may increase the necessary opening force.

In addition, a cutting process may be used to form slots 325a-c of relief 324. For instance, chemical etching, CNC machining, wire EDM, laser cutting, waterjet cutting, or a variety of other processes may be used. In some processes, the cutting process leaves a residue of cut material in passageway 320 that may increase the required opening force. In addition, the width, position, configuration, and length of slots 325a-c may also affect the required opening force.

Accordingly, needle 302 may be adapted for quick and efficient insertion of a guide wire by countering all or a portion of these factors. For instance, the internal surface of needle 302 may be polished or cleaned to remove residue and/or uneven surfaces. For instance, a slurry mixture may be passed through needle 302, or an ultrasonic cleaning procedure may be used. In addition, or in the alternative, needle 302 may be heat treated to remove residue stresses. For instance, an annealing process may be used to soften the material and reduce the required opening force.

Cutting tip 322 may be sharpened by being cut at an angle. For instance, in the illustrated embodiment, an exemplary cutting tip 322 is a lancet point. To create a lancet point, cutting tip 322 is ground at a specific angle (the "bevel angle"), thereby creating a primary grind 327 which is cut at the bevel angle. It will be appreciated any of a variety of bevel angles may be ground. For instance, depending on the application of the needle or the grade of the needle, the bevel may be at or between 12 degrees (an A bevel needle) and 30 degrees (a C bevel needle).

In some embodiments, one or more secondary grinds 328 are further ground into cutting tip 322 to create side bevels. The secondary grinds are on each side of the primary bevel and form a sharp needle point at cutting edge 323. Where secondary grinds 328 connect to primary grind 327, an interface 329 is formed.

In some embodiments, the size, position, configuration and length of slots 325a-c are controlled to provide a desired opening force such as 1.0±0.5 pounds. For instance, as illustrated in FIGS. 3A and 3B, first slot 325a is aligned with the most proximal point E of cutting tip 322, and opposite cutting edge 323. In addition, first slot 325a may be offset from point E, (e.g., angularly or linearly), although in the illustrated embodiment, slot 325a is extends to, and intersects cutting surface 326 of cutting tip 322. As illustrated, in this embodiment, slot 325a does not intersect or otherwise contact cutting edge 323. One feature of such a configuration is that cutting edge 323 at remains sharp so as to easily penetrate a patient's tissue and vascular walls. Another feature of slot 325a which intersects cutting surface 326 is that the opening force may be decreased.

FIGS. 3A and 3B further illustrate a relief 324 which includes second slot 325b and/or third slot 325c rotated and angularly offset from first slot 325a and/or point E of cutting tip 322. For example, when tapered portion 318 is viewed from the distal end (e.g., FIG. 3B), second slot 325b may be positioned at a first angle $\alpha$ from first slot 325a. Similarly, third slot 325c may be positioned at a second angle $\beta$ from first slot 325a. In some embodiments, first angle $\alpha$ and second angle $\beta$ are about equal, although this feature is not limiting and, in other embodiments, first angle $\alpha$ and second angle $\beta$ are different. As may be appreciated in light of the disclosure herein, by varying angle $\alpha$ and angle $\beta$, the opening force can be altered. Accordingly, it is desirable that, in some embodiments, first angle $\alpha$ and second angle $\beta$ be between 45° and 155°. More specifically, either or both of first angle $\alpha$ and second angle $\beta$ may be 115°±10°.

Where second slot 325b and/or third slot 325c are formed in tapered portion 318, they may be intersect or be adjacent primary grind 327, secondary grinds 328, or interface 329. For instance, in the illustrated embodiment, when second slot 325b and third slot 325c are positioned at first angle $\alpha$ and second angle $\beta$, respectively, slots 325b-c are adjacent secondary grinds 328. Accordingly, if primary grind 327 is considered an upper portion, slots 325b-c are positioned at or below interface 329.

Slot 325a, may, however, be positioned at or adjacent primary grind 327 and, in some embodiments, intersects primary grind 327 of cutting surface 326. It should be appreciated, however, the illustrated embodiment is illustrative only, and not necessarily limiting of the present invention. In particular, the positions of slots 325a-c may be varied and can be positioned at virtually any point intersecting or adjacent cutting tip 322, whether adjacent or intersecting primary grind 327, secondary grinds 328, or interface 329.

In addition, and as illustrated, second slot 325b and/or third slot 325c may be proximally offset from cutting surface 326. In particular, second slot 325b and/or third slot 325c may not intersect cutting surface 326. One feature of an offset second slot 325b and/or third slot 325c is the increased strength of cutting tip 322. In particular, where a slot intersects cutting surface 326, the cutting surface may be split into multiple segments that can shift or move. The more slots that intersect the surface, the greater the likelihood that one or more of these segments can be displaced. This may, in some embodiments, reduce the opening force, but may also allow segments to catch on a patient's tissue or vascular walls, or may catch on or interfere with a guide wire.

Accordingly, and although it is not a limiting feature of the present invention, the embodiment illustrated in FIGS. 3A and 3B, includes a relief 324 with slots 325b and 325c proximally offset from cutting surface 326. As will be appreciated, by positioning slots 325b and 325c proximal to cutting surface 326, a horizontal offset a and a vertical offset b are defined. For instance, in FIG. 3A, second slot 325b is proximally offset from cutting surface 326. Horizontal offset a is a horizontal distance between a first, distal end of slot 325a and cutting surface 326. Contrastingly, vertical offset b is the vertical displacement or distance between the first, distal end of slot 325a and cutting surface 326.

The respective lengths of horizontal offset a and vertical offset b can also be controlled and may affect the required opening force of needle 302. As may be appreciated in light of the disclosure herein, moving slots 325b-c in the proximal direction creates a larger offset a and potentially a larger offset b. This may further result in increased strength at distal end 312 of needle 302, inasmuch as more material is present adjacent cutting tip 322. The additional strength may further result in a reduced risk of inadvertent breakage at sharpened tip 322. However, the increased strength may further increase the opening force necessary, and may further require additional expansion of slot 325a or a fracture extending from the distal ends of slots 325b-c to cutting surface 326.

The respective offset lengths a and b may, therefore, be controlled to provide a desirable opening force while also providing a suitable strength to cutting tip 322. For instance, an opening force of 1.0±0.5 pounds may be desired for some applications. For such an application, horizontal offset a and/or vertical offset b may be between 0.002 inch and 0.050 inch. For example, horizontal offset a and/or vertical offset b may be 0.010±0.002 inch.

The width of slots 325a-c may also be controlled to reduce the necessary opening force. In general, a larger width provides greater relief and thus reduces the opening force, while a larger slot decreases the structural strength of distal end 312 of needle 302 and may allow blood or other fluids to escape through needle 302 into the surrounding tissue, or may hinder insertion of a guide wire as the guide wire may try to exit needle 302 though a wider slot. Thus, wide slots 325a-c may create a risk of blood loss, or may reduce the efficiency in inserting a guide wire.

Figure 6:
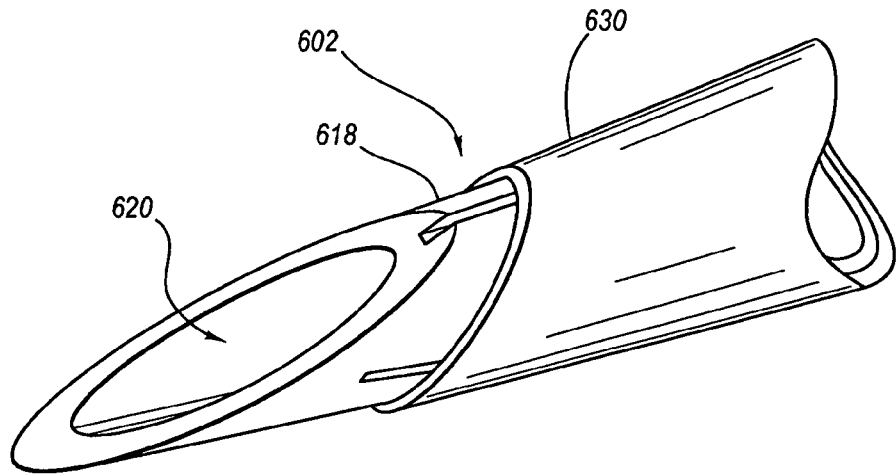
FIG. 6 is a perspective view of the distal end of a tapered medical needle, the distal end having a coating thereon.

In one embodiment, therefore, slots 325a-c are cut at a width between 0.0005 inch and 0.002 inch. For instance, slots 325a-c may be cut at a width of 0.0015 inch. In some circumstances, slots 325a-c may be still be sufficiently wide to allow some blood or fluid to pass therethrough. Accordingly, in some embodiments, such as that illustrated in FIG. 6, a coating 630 may be used applied to the exterior surface of a needle (e.g., needle 602). In this manner, needle 602 is configured to reduce the risk of blood loss. Further, coating 630 can the passage of air into slots or other relief means within needle 602, thereby reducing aspiration. Additionally, coating 630 may extend along tapered portion 318 to or about to cutting tip 322. In this manner, coating 630 may also provide additional strength to cutting tip 322. In still other embodiments, the coating is applied to the sots or an interior surface of a needle.

Any number of materials may be suitable for use as coating 630. For instance, in one embodiment, coating 630 is a flexible material. One feature of a flexible material is that as a guide wire is pushed through passageway 620 and tapered tubular portion 618 radially expands, coating 630 may flex and expand radially so as to allow the guide wire to extend through the needle with no or a negligible effect on the opening force. Representative materials suitable for such an application are numerous and include, for instance, Teflon or a hydrophilic polymer.

Coating 630 may also be used to provide additional beneficial features. For example, in some embodiments, coating 630 includes drug or pharmaceutical components used to promote hemostasis at the vascular access site, or to improve patient comfort. For instance, coating 630 may have drug occlusive properties to promote coagulation. To create such properties, classes of materials including proteins, polypeptides, chemicals, polymers, cationic polymers, and the like may be incorporated by conventional methods. Similarly, a painkiller, anesthetic, or other drug may be applied to coating 630 to improve patient comfort.

Referring again to FIG. 3A, a tapered tubular portion 318 is illustrated which includes a second slot 325b formed therein. For convenience, a discussion of second slot 325b will now be provided, although it should be appreciated that the discussion is equally applicable to slot 325c and/or slot 325a.

As discussed herein, one feature of slot 325b is that it forms all or part of a relief 324 and allows radial expansion of tapered tubular portion 318. In this manner, if a guide wire is inserted into passageway 320 of needle 302, tapered tubular portion can expand, if necessary, to accommodate a variety of sizes of guide wires. The length of second slot 325b may also be varied to control and allow for a desired radial expansion. For instance, in the illustrated embodiment, second slot 325b has a length such that a proximal end of second slot 325b is proximal to junction A. In this manner, relief is provided along all or substantially all of tapered portion 318 between a tapered portion 318 and a straight portion 317, thus facilitating expansion of all or substantially all of tapered tubular portion 318.

In the illustrated embodiment, a major length of tapered portion 318 may be defined as the horizontal distance between Junction A and Point B, a minor length of tapered portion 318 may be defined as the horizontal distance between Junction A and Point E, and a tip length may be defined as the horizontal distance between Point B and Point E. In some embodiments, the length of slot 325b is equal to or greater than the tip length. In other embodiments, the length of slot 325b is less than the major length and greater than the minor length. In still other embodiments, the length of slot 325b is equal to or greater than the major length.

Accordingly, in light of the teachings herein, it may be appreciated that the length of slot 325b may be increased or decreased as desired, such that the proximal and distal ends of slot 325b can be positioned at a variety of locations. In particular, the proximal end of slot 325b may also be about at or distal to Junction A. Alternatively, while the illustrated embodiment illustrates a proximal end of slot 325b which is only slightly proximal to junction A, slot 325b may extend a substantial length along straight portion 317, and may thus allow straight portion 317 to radially expand.

In some embodiments, the proximal ends of two or more of slots 325a-c are aligned so as to be approximately the same distance proximal (or distal) to junction A. In other embodiments, however, the proximal ends of slots 325a-c are not aligned, but are staggered. One feature of a staggering the proximal end is that needle 302 may have added resistance to fracture. In particular, as a guide wire is extended through passageway 320, or as distal end 312 of needle 302 otherwise expands, the expansion stresses needle 302 at the proximal ends of slots 325a-c. By staggering the positions of the proximal ends of slots 325a-c the stresses can also be staggered, thereby possibly reducing the risk that needle 302 will inadvertently fracture under the stress caused by expanding to allow a guide wire therethrough.

Figure 4A:
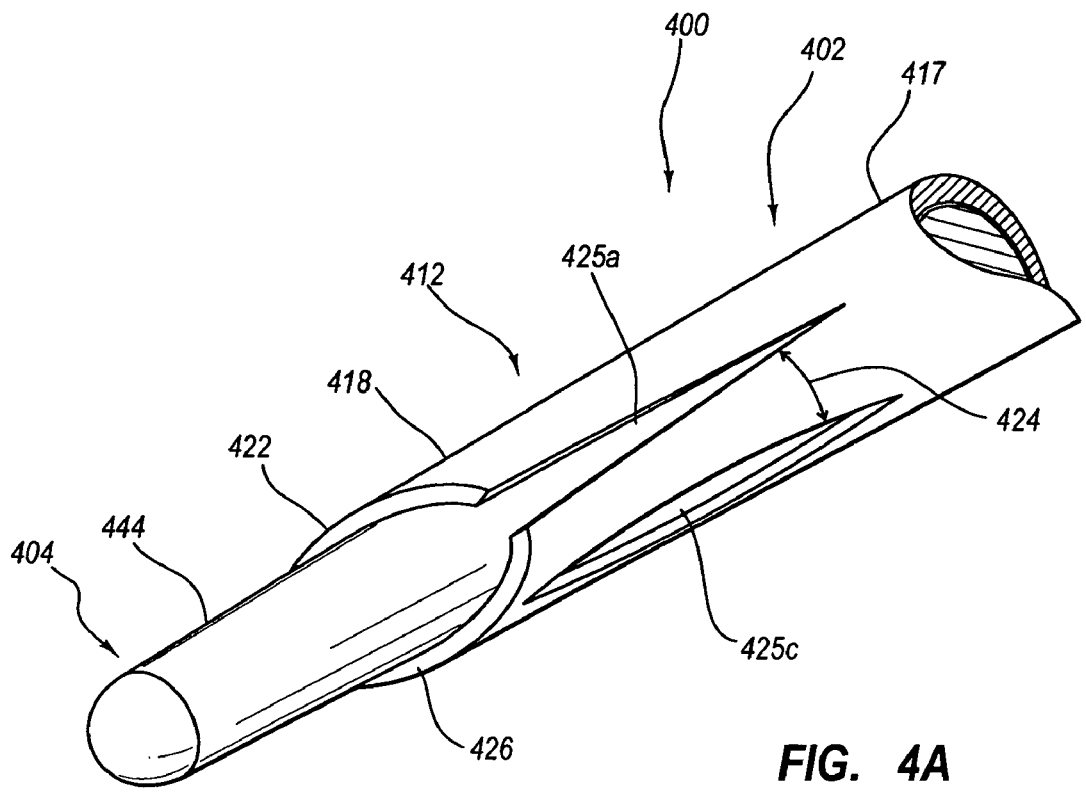
FIG. 4A is a perspective view of a guide wire insertion system in which a guide wire is positioned within an expanded tapered needle.
Figure 4B:
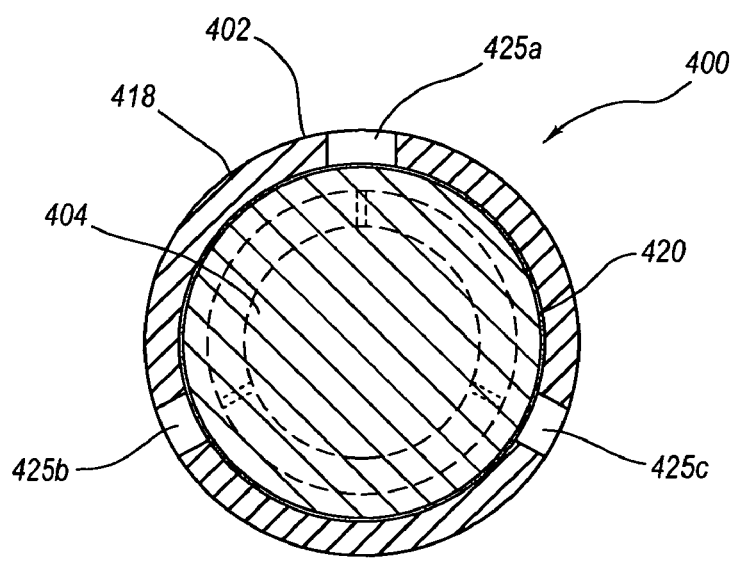
FIG. 4B is a cross-sectional view of the guide wire insertion system of FIG. 3B.

Turning now to FIGS. 4A and 4B, an exemplary needle and guide wire assembly 400 is illustrated in which a guide wire 404 is inserted into a passageway 420 of an expanded needle 402. In the illustrated embodiment, needle 404 includes a relief 424 comprising a plurality of slots 425a-c, and the diameter of guide wire 404 is greater than the internal diameter of an unexpanded tapered portion 418. Thus, as guide wire 404 is inserted into tapered portion 418, relief 424 acts to allow the internal diameter of tapered portion 418 to expand and accommodate the larger guide wire 404.

In the illustrated embodiment, for example, the width of slots 425a-c increases from their unexpanded width (illustrated in phantom lines in FIG. 4B) when guide wire 404 is extended through the interior of tapered portion 418. The increased width of the slots, in turn, results in an increase in both the internal and outer diameters of tapered portion 418, thereby radially expanding tapered portion 418. In particular, and as illustrated in FIG. 4B, which provides a cross-sectional view of tapered portion 418 of FIG. 4B, when guide wire 404 is inserted into passageway 420, the diameters of tapered portion 418 expand from their unexpanded size (illustrated in phantom lines) to a larger, radially expanded diameter. In some embodiments, the internal diameter of tapered portion 418 after expansion is about equal to the diameter of guide wire 404.

Figure 5A:
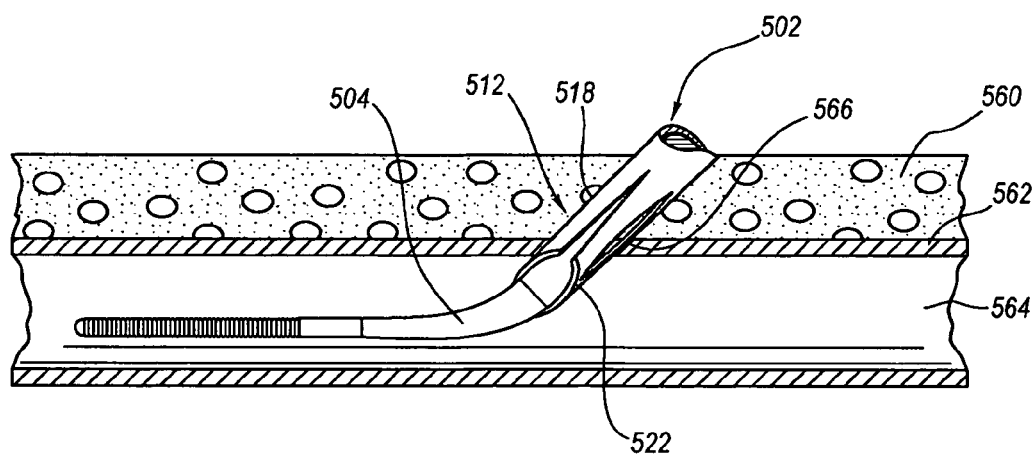
FIG. 5A is a cross-sectional view illustrating insertion of a guide wire into a patient through a tapered needle.
Figure 5B:
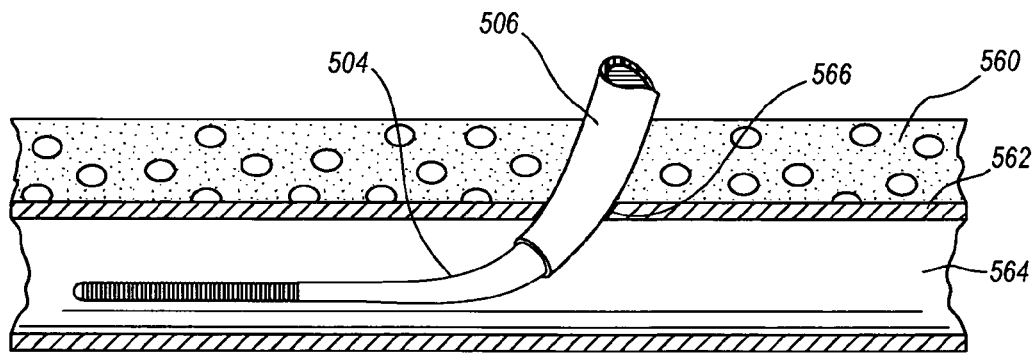
FIG. 5B is a cross-sectional view illustrating placement of a catheter over the guide wire illustrated in FIG. 5A.

Referring now to FIGS. 5A and 5B, an exemplary method for installing a medical device such as a catheter is illustrated. In FIG. 5A, for example, under the direction of a physician, a needle 502 having a tapered distal end 512 and cutting tip 522 is cuts into a patient's tissue 560 and penetrates a vascular wall 562 to enter vascular lumen 564. As cutting tip 522 is passed through vascular wall 562, a vascular access site 566 is created. As described herein, when vascular access site 566 created, its size corresponds to the outer diameter of needle 502 at cutting tip 522. Thereafter, as needle 502 is further inserted into lumen 564, vascular wall 562 expands and stretches to accommodate the increased diameter of tapered portion 518.

Similarly, as guide wire 504 is inserted into needle 502, and tapered portion 518 expands to accommodate guide wire 504, tapered portion 518 presses against vascular wall 562, thereby causing it to stretch and further increase the size of vascular access site 566. Guide wire 504 may then be inserted into lumen 564. Thereafter, as illustrated in FIG. 5B, needle 502 may be extracted, leaving guide wire 504 inside lumen 564. When needle 502 is extracted, the size of vascular access site 566 may be reduced. In particular, because the outer diameter of expanded needle 502 is greater than the diameter of guide wire 504, vascular access site 566 can shrink down to about the size of inserted guide wire 504.

Thereafter, a medical device 506 can be inserted into lumen 564 using guide wire 504. In particular, medical device 506 (e.g., a catheter) can be placed on the same guide wire 504 passed through tapered needle 502. One advantage of using a tapered needle 502 which is expandable to accommodate guide wire 504 is that a physician may quickly and efficiently install medical device 506 without the need to place a coaxial dilator or to install a second, larger guide wire. Moreover, because tapered needle 502 is expandable, the size of vascular access site 566 is reduced.

As illustrated, guide wire 504 directs medical device 506 through tissue 560 to vascular wall 562. Upon reaching vascular access site 566, medical device 506 is pushed into lumen 564, thereby causing vascular wall 562 to stretch and increase the size of vascular access site 566. Medical device 506 may then be directed along guide wire 504 to a lesion or other desired site within lumen 564.

In some embodiments, such as that illustrated in FIG. 5B, medical device 506 may, therefore, be inserted into lumen 564 without the use of a dilator and/or introducer. In this manner, the ease and efficiency of installing medical device 506 is increased. In other embodiments, however, an introducer or dilator may be used to expand vascular access site 566 or otherwise facilitate insertion of medical device 506.

As should be appreciated in light of the teachings herein, the present invention contemplates a tapered medical needle having a relief in a distal end to facilitate expansion of the distal end so as to receive a guide wire that is larger than the un-expanded diameter of all or a portion of the distal end. Any number of relief means are contemplated and suitable for this purpose. For instance, as discussed herein, one or more narrow slots may be formed in a tapered portion of a needle so as to facilitate radial expansion of the needle. FIGS. 7A-7E illustrate further exemplary embodiments of a relief which are expressly contemplated for use with the present invention. It will be appreciated that the illustrated embodiments are exemplary only, and are in no way intended to limit the type of relief usable with the present invention.

Figure 7A:
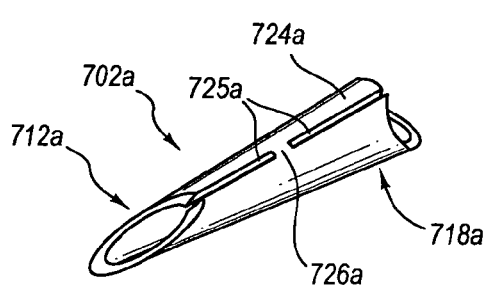
FIGS. 7A-7D illustrate various alternative embodiments of a relief for facilitating radial expansion of a needle.

In FIG. 7A, for example, an exemplary needle 702a is illustrated, which includes a tapered portion 718a and a relief 724a to facilitate radial expansion of tapered portion 718a. In this embodiment, relief 724a includes a slot 725a. For clarity, a single slot 725a is illustrated, although it will be appreciated that this embodiment may be combined with one or more other embodiments disclosed herein. Accordingly, and as one example, relief 724a may include multiple slots similar to or identical to slot 725a.

In this embodiment, relief 724 includes one or more slots 725a. Slot 725a may be a continuous cut along tapered portion 718a or may have, as illustrated, one or more bridge portions 726a dividing slot 725a into a plurality of portions. A single bridge 726a may be included, or multiple bridges may be used along the length of slot 725a. Bridge 726a may be of any suitable length. For instance, bridge 726a may be at or between 0.0005 to 0.01 inch long, including at or about 0.002 to 0.003 inch.

Bridge 726a may provide structural strength to distal end 712a, thereby helping needle 702a maintain its integrity when inserted into a patient. Once needle 702a is inserted, bridge 726a may provide little or no change to the opening force required to expand needle 702a (when compared to a continuous cut). As a guide wire is inserted, bridge 726a may even fracture, such that slot 725a becomes a single, continuous slot.

Figure 7B:
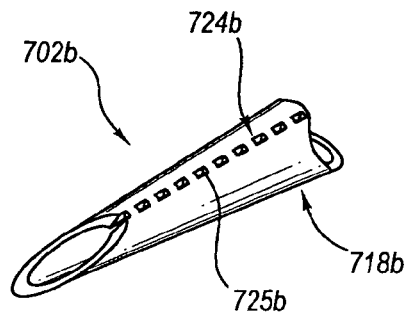

FIG. 7B illustrates another alternative embodiment of a needle 702b having a relief 724b in a distal tapered end 718b. In this embodiment, relief 724b comprises a perforation 725b, which acts similar to the slot 725a of FIG. 7A.

Figure 7C:
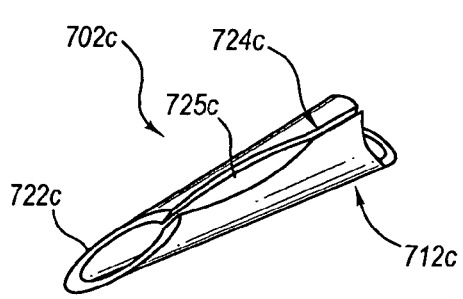

FIG. 7C illustrates yet another embodiment of a needle 702c having a relief 724c at an expandable distal end 712c. In this embodiment, relief 724c includes a slot 725c, where the width of slot 725c varies along its length. In particular, in this embodiment, the width of slot 725c is largest at or adjacent cutting tip 722c. At the cutting tip, needle 702c has its smallest size and the greatest amount of expansion is necessary when a larger guide wire is inserted. Accordingly, the increased width of slot 725c facilitates radial expansion of distal end 712c where the greatest expansion is required.

Figure 7D:
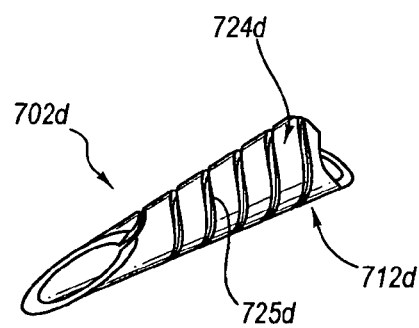

FIG. 7D illustrates yet another embodiment of a relief 724d which may be used to allow a narrow portion of needle 702d to expand and receive a larger guide wire. In this embodiment, a spiral slot 725d is formed at distal end 712d of needle 702. As a guide wire is inserted into needle 702d, the width of slot 725d increases, thereby also increasing the diameter of needle 702d.

As will be appreciated, the foregoing embodiments are exemplary only and not limiting of the present invention. For instance, while the illustrated embodiments of FIGS. 7A-7D illustrate a variety of reliefs which include slots and perforations, it is not necessary that a slot or perforation be used. For instance, in one embodiment, a relief may be formed by using a flexible, deformable material which stretches as a guide wire is inserted inside the needle. In addition, it is not necessary that any slot or perforation extend through the full thickness of a needle wall. For instance, a relief may include a score. For instance, as illustrated in greater detail in FIG. 6, one or more scores may be included in which the score extends only partially through a needle wall. Such a score may provide additional structural strength to the needle when compared to a slot. Further, when a guide wire is inserted, the reduced amount of material may allow for greater flexibility in the needle, or may fracture as necessary to accommodate a guide wire.

In addition, it should be appreciated in light of the disclosure herein, that a needle according to the present invention can have any of a variety of cross-sectional shapes and areas. For instance, tubular portion of the needle, including a straight or tapered portion, may have a circular, triangular, oval, square, diamond, or other cross-sectional shapes. In some embodiments, the cross-sectional shape may also provide a mechanical advantage to the needle. For instance, by way of representation and not limitation, the opening force of a needle may be decreased, or the axial strength of the needle may be increased, depending on the cross-section of the needle. Optionally, an additional mechanical advantage may be obtained by using the guide wire as a ramp. In particular, as discussed herein, the guide wire may be tapered such that as the guide wire is inserted into a tapered needle, the needle can be gradually expanded and ramps up to the full expansion necessary to receive the guide wire.

Inasmuch as the present invention is not limited to circular cross sections, terms "diameter" and "cylinder", as used herein, should not be limited to circular or oval cross-sectional shapes, and also refer to other geometries. In particular, as it is used herein, the term "diameter" refers to the diameter of the largest circle that can be inscribed within any geometric shape. Thus, the diameter of a square is equal to its length and height, the diameter of a rectangle is equal to the smaller of its length and height, and so on.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A medical device comprising:
    a tapered guide wire comprising a first length and a second length, wherein said first length has a diameter and said second length has a diameter that is larger than said diameter of said first length; and
    a medical needle adapted to access the interior of a patient's vessel by insertion of the medical needle therein and facilitate insertion of said tapered guide wire into the interior of the patient's vessel, the medical needle comprising a substantially rigid tapered tube portion having a first end, a second end, and a channel extending therethrough between said first end and said second end, said channel having a first diameter at said first end of said substantially rigid tapered tube portion, wherein said first diameter of said channel allows for at least a portion of said first length of said tapered guide wire to be passed through said channel while substantially maintaining said first diameter of said channel, said substantially rigid tapered tube portion comprising:
        a sharpened distal end portion disposed at said first end of said substantially rigid tapered tube portion, said sharpened distal end portion defining a cutting surface adapted to create an incision in a vessel wall of a subject to facilitate insertion of said sharpened distal end portion into the interior of a patient's vessel, wherein said channel extends through said sharpened distal end portion to define an opening therein, wherein at least a portion of said first length of said tapered guide wire can be passed through said channel, through said opening in said sharpened distal end portion, and introduced into the interior of the patient's vessel while said channel substantially maintains said first diameter at said first end;
        one or more slots adapted to facilitate radial expansion of said channel from said first diameter of said channel to at least said diameter of said second length of said tapered guide wire to enable advancement of at least a portion of said second length of said tapered guide wire through said channel, through said opening in said sharpened distal end portion, and into the interior of the patient's vessel without using a separate introducer or dilator.

2. The medical needle of claim 1, wherein an outside diameter at said second end is greater than an outside diameter at said distal end portion.

3. The medical needle of claim 1, wherein a first slot of said one or more slots intersects said cutting surface, and wherein a second slot and a third slot are each offset from said cutting surface, wherein the offset of each of said second and third slots enables said substantially rigid tapered tube portion to radially expand to allow for at least a portion of said second length of said tapered guide wire to pass through said channel and through said opening in said cutting surface while substantially maintaining the continuity of said cutting surface.

4. The medical needle of claim 3, further comprising a relief on said tapered tube portion, said relief facilitating radial expansion of said tapered tube portion.

5. The medical needle of claim 4, wherein said relief comprises one or more of a group consisting of: a flexible material, a slot, a perforation, a spiral, and a score.

6. The medical needle of claim 1, wherein said one or more slots comprises a first slot formed proximate said sharpened distal end.

7. The medical needle of claim 1, wherein said one or more slots intersect said cutting surface.

8. The medical needle of claim 1, wherein said tapered tube portion comprises a plurality of slots proximate said distal end portion, said plurality of slots being configured to facilitate expansion of at least a portion of said tapered tube portion.

9. The medical needle of claim 1, wherein said cutting surface has a primary grind, at least one secondary grind, and an interface between said primary grind and said at least one secondary grind, and wherein the medical needle further comprises:
   a first slot adjacent said primary grind;
   a second slot adjacent one of said interface or said at least one secondary grind; and
   a third slot adjacent one of said interface or said at least one secondary grind.

10. The medical needle of claim 9, wherein at least one of said second slot and said third slot is proximally offset a first distance from said cutting surface.

11. The medical needle of claim 10, wherein said first distance is about 0.01 inch.

12. The medical needle of claim 10, wherein one of said second slot and said third slot does not intersect said cutting surface.

13. The medical needle of claim 9, wherein at least one of said second slot and said third slot is offset a second distance from said cutting surface.

14. The medical needle of claim 13, wherein said second distance is about 0.01 inch.

15. The medical needle of claim 1, wherein at least three slots are formed adjacent said cutting surface of said distal end portion, a second slot being offset from a first slot at a first angle, and a third slot being offset from said first slot at a second angle, wherein said second angle is in a direction opposite said first angle, and wherein one or more of said first angle and said second angle is between about 110° and 120°.

16. The medical needle of claim 15, wherein said first angle and said second angle are about 115°.

17. The medical needle of claim 1, further comprising a coating on at least a portion of said tapered tube portion, wherein said coating is adapted to inhibit blood or air leakage through the one or more slots.

18. The medical needle of claim 1, wherein said one or more slots are coated with a material adapted to inhibit blood or air leakage through said one or more slots when said sharpened distal end portion is inserted into a patient's vessel.

19. A medical device comprising:
   a tapered guide wire comprising a first diameter along a first portion and a second diameter along a second portion, wherein said second diameter is larger than said first diameter; and
   a medical needle adapted to (i) secure and confirm access to the interior of a vessel, (ii) enable passage of at least a portion of said first portion of said tapered guide wire through said medical needle and into the interior of the vessel to facilitate selective positioning of said first portion of said tapered guide wire within the interior of the vessel, and (iii) radially expand to allow for advancement of at least a portion of said second portion of said tapered guide wire through said medical needle and into the interior of the vessel, said medical needle comprising:
      a substantially rigid tapered tube having a channel extending therethrough from a first end to a second end, said first end of said tapered tube comprising a sharpened distal portion adapted to create an incision in a wall of the vessel and be inserted into the interior of the vessel, said channel extending through said sharpened distal portion to define an opening in said sharpened distal portion, said channel having a diameter at said opening to enable at least a portion of said first portion of said tapered guide wire to pass through said channel, out of said opening, and be introduced into the interior of the vessel to facilitate selective positioning of said first portion of said tapered guide wire within the vessel; and
      a first slot and one or more secondary slots that facilitate radial expansion of said tapered tube to allow for advancement of at least a portion of said second portion of said tapered guide wire through said channel and into the vessel, wherein:
         said first slot extends along a length of a substantial portion of said tapered tube, said first slot having a first end that intersects said sharpened distal portion before said tapered tube radially expands to allow for advancement of said second portion of said tapered guide wire through said channel; and
         said one or more secondary slots extend along a length of a substantial portion of said tapered tube, said one or more secondary slots being angularly offset from said first slot, at least one slot of said one or more secondary slots having a first end adjacent to and linearly offset from said sharpened distal portion before said tapered tube radially expands to allow for advancement of said second portion of said tapered guide wire through said channel,
      wherein said first slot and said one or more secondary slots comprise a coating adapted to inhibit blood or air leakage through said first slot and said one or more secondary slots when said sharpened distal portion is inserted into the vessel, and wherein said medical needle is adapted to facilitate insertion of at least a portion of each of said first and second portions of said tapered guide wire into the vessel of a subject while said sharpened distal portion is positioned within the vessel of the subject.

20. A medical needle as recited in claim 19, wherein said first slot and said one or more secondary slots facilitate radial expansion of said tapered tube from said first diameter to said second diameter when said medical device is passed through said tapered tube with a force of between about 0 and about 2.5 pounds.

21. A medical needle as recited in claim 19, wherein said first slot and said one or more secondary slots facilitate radial expansion of said tapered tube from said first diameter to said second diameter when said medical device is passed through said tapered tube with a force of between 0.5 and 1.5 pounds.

22. A medical needle as recited in claim 19, wherein said one or more secondary slots comprise a first secondary slot and a second secondary slot.

23. A medical needle as recited in claim 22, wherein said first and second secondary slots are angularly offset from one another.

24. The medical needle of claim 19, wherein said first slot and said one or more secondary slots facilitate radial expansion of said tapered tube to allow for advancement of said at least a portion of said second portion of said tapered guide wire through said channel and into the vessel while substantially maintaining the continuity of said sharpened distal portion.

* * * * *